US00PP27138P2

(12) United States Plant Patent
Probst

(10) Patent No.: US PP27,138 P2
(45) Date of Patent: Sep. 6, 2016

(54) ***COREOPSIS* PLANT NAMED 'DAYBREAK'**

(50) Latin Name: ***Coreopsis* hybrid**
Varietal Denomination: Daybreak

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 120 days.

(21) Appl. No.: 14/120,622

(22) Filed: Jun. 10, 2014

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

Digger 2013 New Varieties Showcase retrieved on Nov. 19, 2015, retrieved from the Internet at <http://www.upshoothort.com/wp-content/uploads/2013/08/Digger2013NewVarieties.pdf> pp. 1, 100-112.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Daybreak' that is characterized by its compact plant habit reaching about 30 cm in height and 50 cm in spread, its prolific blooming habit from late June until frost in Connecticut, its large inflorescences with ray florets that are golden yellow in color with very large red eye zones that expand to nearly cover the entire ray floret in cooler temperatures, its near sterility when grown under typical garden conditions without the requirement for deadheading of spent blooms for continuous bloom and its ability to be readily propagated by stem cuttings throughout the growing season.

2 Drawing Sheets

Botanical classification: *Coreopsis* hybrid.
Variety denomination: 'Daybreak'.

BACKGROUND OF THE INVENTION

The present invention relates to a new and distinct cultivar of *Coreopsis* plant, botanically of hybrid origin and known as *Coreopsis* 'Daybreak' and will be referred to hereinafter by its cultivar name, 'Daybreak'. The new cultivar of *Coreopsis* is an herbaceous perennial grown for landscape and container use.

The new Invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms.

The Inventor made a controlled cross in July of 2009 in his test garden in Hubbardston, Mass. between an unnamed plant from his breeding program, ref. no. Q1 07-1, as the female parent and pollen that was pooled from a variety of unnamed plants from his breeding program as the male parent (all nearly sterile). The exact characteristics of the pollen parent are therefore unknown. 'Daybreak' was selected in September of 2010 as a single unique plant amongst the resulting seedlings.

Asexual propagation of the new cultivar was first accomplished by stem cuttings under the direction of the Inventor in Kensington, Conn. in September of 2010. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Daybreak' as a unique cultivar of *Coreopsis*.

1. 'Daybreak' exhibits a compact plant habit reaching about 30 cm in height and 50 cm in spread
2. 'Daybreak' exhibits a prolific blooming habit from late June until frost in Connecticut.
3. 'Daybreak' exhibits large inflorescences with ray florets that are golden yellow in color with very large red eye zones that expand to nearly cover the entire ray floret in cooler temperatures.
4. 'Daybreak' is relatively sterile when grown under typical garden conditions and does not require deadheading of spent blooms for continuous bloom.
5. 'Daybreak' is readily propagated by stem cuttings throughout the growing season.

The female parent of 'Daybreak', Ref. No. Q1 07-1, differs from 'Daybreak' in being highly fertile and produces full seed heads that result a one month blooming period without deadheading. 'Daybreak' can be most closely compared to *Coreopsis* cultivars 'Cosmic Eye' (U.S. Plant Pat. No. 22,601) and 'Little Sundial' (U.S. Plant Pat. No. 18,460). 'Cosmic Eye' is similar to 'Daybreak' in having a compact plant habit and in having large flowers with a large eye zone. 'Cosmic Eye' differs from 'Daybreak' in having ray florets that are bright yellow in color with a burgundy eye and in being difficult to propagate by stem cutting once flowering commences. 'Little Sundial' is similar to 'Daybreak' in having a compact plant habit and in having golden yellow ray florets. 'Little Sundial' differs from 'Daybreak' in having a bun shaped plant habit with less spread, therefore taking longer to fill in a one-gallon container and in having inflorescences with ray florets with a very small red eye zone.

BRIEF DESCRIPTION OF THE DRAWING

The accompanying colored photographs illustrate the overall appearance and distinct characteristics of the new *Coreopsis*.

The photograph in FIG. 1 was taken in September of a 1 year-old plant as grown outdoors in Kensington, Conn. and sheared once in July (to remove spent blooms for photographic purposes).

Figure 1:
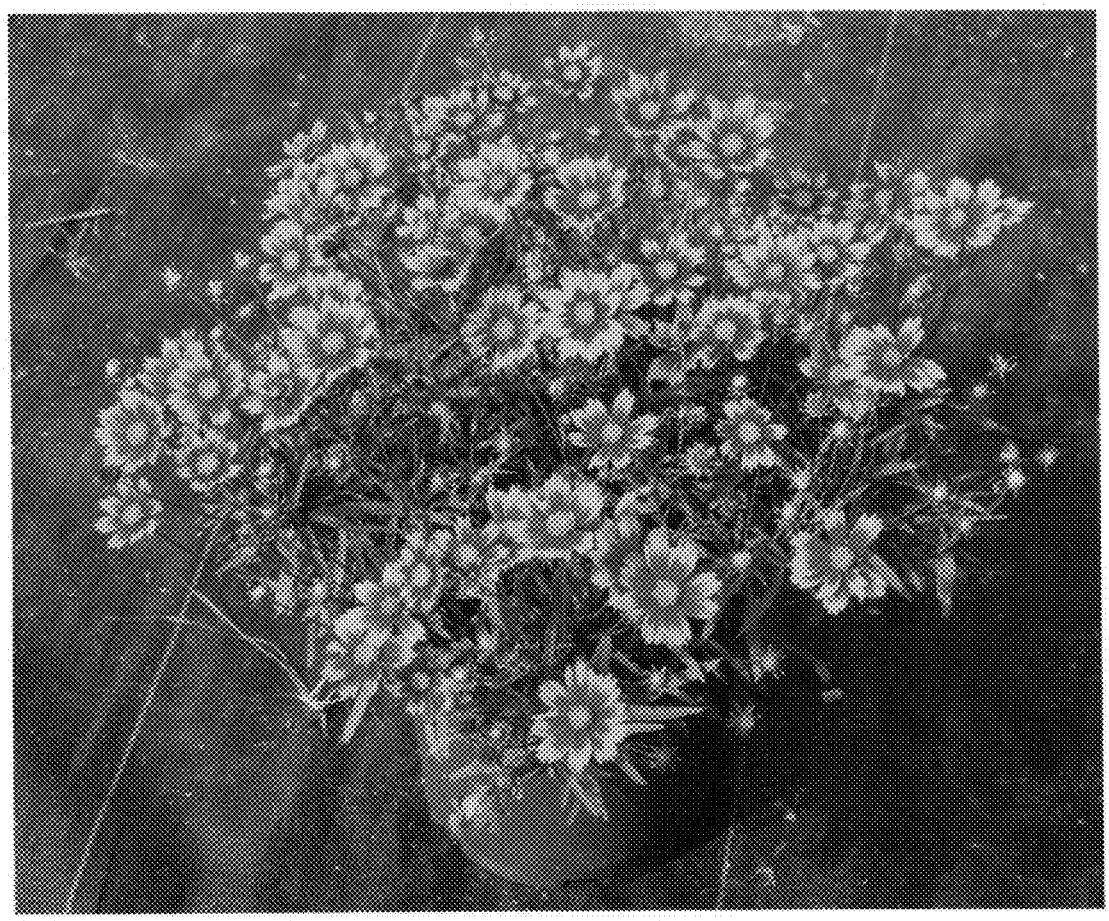
FIG. 1 shows the overall growth and flowering habit of 'Daybreak' with heavy bloom still present in September.
Figure 2:
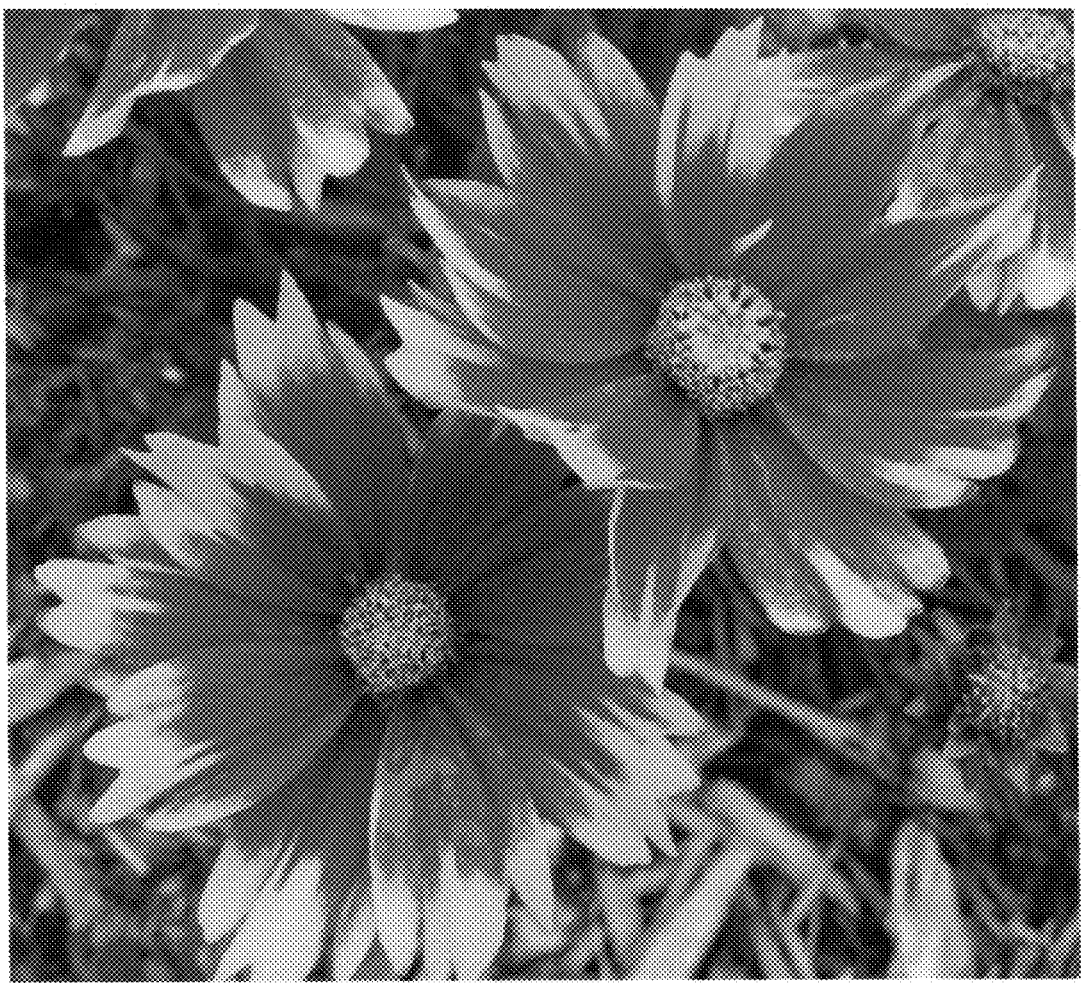

The photograph in FIG. 2 was taken of a one year-old plant of 'Daybreak' as grown in a garden in Mount Vernon, Wash. The photograph in FIG. 2 provides a close-up view of an inflorescence of 'Daybreak' when grown under cool conditions with the eye zone expanded to cover most of the ray florets.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as recorded from five month-old plants (from a liner) of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June until frost in Kensington, Conn.

*Plant type*.—Herbaceous perennial.

*Plant habit*.—Clump-forming and compact.

*Height and spread*.—Reaching about 30 cm in height and 50 cm in spread.

*Cold hardiness*.—At least to U.S.D.A Zone 5.

*Diseases resistance*.—Relatively resistant to Powdery Mildew in comparison to cultivars of *Coreopsis grandiflora*.

*Root description*.—Fibrous, fine and well-branched.

*Propagation*.—Terminal stem cuttings.

*Growth rate*.—Vigorous but retains a compact habit.

Stem description:

*Shape*.—Oval, solid.

*Stem color*.—Young; 144A, mature; 143A, bark is a blend of 197A and 199A.

*Stem size*.—Main stem (including peduncles) averages 20 cm in length and 3 mm in width with lateral branches an average of 3 cm in length (excluding peduncles) and 2 mm in width.

*Stem surface*.—Glabrous when young, ridged and dull when mature.

*Branching habit*.—Up to 6 basal branches with 6 secondary branches, branch internode is variable but up to 2.5 cm and arise opposite at nodes.

Foliage description:

*Leaf division*.—Simple.

*Leaf margins*.—Entire with a few tri-lobed all with slight undulations.

*Leaf size*.—Tri-lobed; up to 6 cm in length and 1.5 cm in width when mature with center lobe an average of 4 cm in length and 5 mm in width and secondary lobes an average of 1.5 cm in length and 2 mm in width, entire; 5 cm in width and 5 mm in width.

*Leaf shape*.—Lanceolate with lanceolate lobes when tri-fid.

*Leaf base*.—Attenuate.

*Leaf apex*.—Narrowly acute.

*Leaf venation*.—Pinnate, not prominent, coloration same as leaf on both surfaces.

*Leaf attachment*.—Sessile.

*Leaf arrangement*.—Opposite.

*Leaf surface*.—Upper and lower surface glabrous and dull.

*Leaf color*.—Young and mature upper surface; N137A, young and mature lower surface; 138A.

Flower description:

*Inflorescence type*.—Composite with ray florets surrounding disk florets in the center, forming a radiant head, inflorescences are borne on terminals arising from leaf axils.

*Lastingness of inflorescence*.—About 10 days until senescence of ray florets, bracts and disk florets are persistent.

*Fragrance*.—None.

*Quantity of inflorescences*.—An average of 14 per lateral branch, blooms are continuously produced until frost.

*Inflorescence size*.—Up to 5 mm in depth and up to 6.5 cm in diameter with disk portion up to 1 cm in diameter.

*Inflorescence buds*.—Average of 5 mm in depth and 8 mm in diameter, shape is spherical, color is a blend of 15A and slight overlay of 165B.

*Peduncle*.—Strong, average of 2 cm in length and 2 mm in diameter, 146A in color, glabrous surface.

*Pedicle*.—Strong, average of 11 cm in length and 1 mm in diameter, 146A in color, glabrous surface.

Involucral bracts:

*Bract number*.—8 inner bracts and 8 outer bracts.

*Bract arrangement*.—Un-fused and somewhat reflexed when flower is fully open and becoming horizontal after ray florets drop.

*Bract size*.—Outer bracts; up to 5 mm in length and 2 mm in width, inner bracts; 7 mm in length and 3 mm in width.

*Bract color*.—Outer bracts; 138A on both surfaces, inner bracts; 151A with base 146B and translucent.

*Bract texture*.—All surfaces glabrous.

*Bract apex*.—Acute.

*Bract base*.—Truncate.

*Bract margins*.—Entire.

*Bract shape*.—Lanceolate.

Ray florets (pistillate):

*Number.*—10.

*Shape*.—Oblanceolate, appearance of three longitudinal sections with center section longer, slightly overlapping and apex of each free.

*Size*.—An average of 2 cm in length and 8 mm in width.

*Apex*.—3-lobed with center lobe pointed emarginate and side lobes pointed.

*Base*.—Cuneate.

*Margins*.—Entire on sides, lobed at apex.

*Aspect*.—Held slightly upward.

*Texture*.—Both surfaces glabrous.

*Color*.—Upper and lower surface when opening and fully open; base is a blend of 42A and 46A, mid section to tip is 21A, upper and lower surface when opening and fully open; 14A with light striping from the base to mid section of N34A.

Disk florets (perfect):

*Number.*—200.

*Shape*.—Tubular, corolla is fused, flared at apex.

*Size*.—About 5 mm in length and 1 mm in width.

*Color*.—En masse; 18A, corolla; base (tube) is 11B in color, flared portion is 17A and translucent.

*Receptacle*.—About 5 mm in diameter and 2 mm in depth, 144C in color.

Reproductive organs:

*Presence*.—Disk florets are perfect, ray flowers are pistillate.

*Gynoecium.*—1 Pistil, 4 mm in length, style is very fine and about 11A in color and translucent, bifid pilose stigma is 23A in color with branches about 1 mm in length and recurved, ovary is 2 mm in length, 4 mm in width, inferior, and 150B in color.

*Androcoecium.*—5 stamens, fused into tube surrounding style, 1 mm in length and 0.5 mm in width, about 200B in color, no pollen was observed.

*Fruit/seed*.—No fruit or seed development was observed, plants have been observed to be nearly sterile.

It is claimed:

1. A new and distinct cultivar of *Coreopsis* plant named 'Daybreak' as herein illustrated and described.

* * * * *